(12) United States Patent
Caffey

(10) Patent No.: US 6,271,670 B1
(45) Date of Patent: Aug. 7, 2001

(54) METHOD AND APPARATUS FOR DETECTING EXTERNAL CRACKS FROM WITHIN A METAL TUBE

(75) Inventor: Thurlow W. H. Caffey, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/246,262

(22) Filed: Feb. 8, 1999

Related U.S. Application Data

(60) Provisional application No. 60/074,083, filed on Feb. 9, 1998.

(51) Int. Cl.[7] .................................................. G01R 27/04
(52) U.S. Cl. ........................................... 324/642; 324/644
(58) Field of Search ...................................... 324/644, 238, 324/754, 716, 331, 219, 220, 239, 240, 642, 637, 638

(56) References Cited

PUBLICATIONS

Zetec, Inc., 1370 NW Mall St., Issaquah, WA 98027–0140; "*Waste Storage Tank Probe/Scanner—Remote Field Testing (RFT) Probes*" (undated) No month/year available.

Tuboscope Pipeline Services, "*Introduction to Pipeline Services—Survey Tool Operation; Trures*" (undated), pp. 2, 16–18 No month/year available.

D. R. Diercks, W. J. Shack, and J. Muscara, "*Overview of Steam Generator Tube Degradation and Integrity Issues,*" Argonne National Laboratory (undated) No month/year available.

D. S. Kupperman and S. Bakhtiari, "*Characterization of Flaws in a Tube Bundle Mock–Up for Reliability Studies,*" Argonne National Laboratory (undated) No month/year available.

S. Bakhtiari and D. S. Kupperman, *Modeling of Eddy current Probe Response for Steam Generator Tubes*, Argonne National Laboratory (undated) No month/year available.

Thurlow W. H. Caffey, "*A Tool to Detect External Cracks from within a Metal Tube,*" SAND 97–0170 (Printed Jan. 1997, Published Feb. 20, 1997).

Thurlow W. H. Caffey, "*Elements of a Continuous–Wave Borehole Radar,*" SAND 97–1995 (Printed Aug. 1997).

*Primary Examiner*—Safet Metjahic
*Assistant Examiner*—Vincent Q. Nguyen
(74) *Attorney, Agent, or Firm*—Russell D. Elliott

(57) ABSTRACT

A method and tool using a continuous electromagnetic wave from a transverse magnetic-dipole source with a coaxial electric-dipole receiver is described for the detection of external sidewall cracks and other anomalies in boiler tubes and other enclosures. The invention utilizes the concept of radar backscatter rather than eddy-currents or ultrasound, which are sometimes used in prior art crack-detection methods. A numerical study of the distribution of the fields shows that the direct transmission from the source to the receiver is reduced from that in free space. Further, if the diameter of the receiver dipole is made sufficiently small, it should be possible to detect cracks with a scattering loss of up to −40 dB in thin-walled boiler tubes.

26 Claims, 9 Drawing Sheets

METHOD AND APPARATUS FOR DETECTING EXTERNAL CRACKS FROM WITHIN A METAL TUBE

This application claims the benefit of U.S. Provisional Application No. 60/074,083, filed Feb. 9, 1998 Provisional application expired, and which is herein incorporated by reference in its entirety.

GOVERNMENT RIGHTS

This invention was made with support from the United States Government under Contract DE-AC04-96AL85000 awarded by the U.S. Department of Energy. The Government has certain rights in this invention.

BACKGROUND OF THE INVENTION

1. Field of the Invention

This invention pertains generally to detecting cracks and other anomalies in tubes such as steam tubes used in boiler applications. A method and apparatus are disclosed in which, in the preferred embodiment, a transverse magnetic-dipole source positioned inside a tube generates a continuous electromagnetic wave and electric field parallel to the axis of the tube. The wave reflects off the external wall of the tube and returns to a coaxial electric-dipole receiver. The transmitting and receiving antennas are designed and positioned to minimize crosstalk and at the same time distinguish cracks and other anomalies in the tube based on the return signal.

2. Description of the Related Art

Historically, and even to the present day, the major cause of boiler outages is the degradation of the steam tubes by which heat is extracted from the boiler. Although there is deposition and corrosion upon the internal surfaces of the tubes, the principal cause of failure is by the development of exterior cracks. Of course, when a boiler is otherwise down for repair, the exteriors of all apparently satisfactory tubes are inspected for cracking. Unfortunately, some cracks may not be discovered because the exterior surfaces are more or less covered by combustion or corrosion products. An inspection tool that could be passed through a boiler tube, and detect an unseen sidewall crack from within, would increase the intervals between boiler outage and provide substantial cost savings.

Other approaches for detecting cracks in metal and other structures have been described which utilize electromagnetic waves. Unlike the invention disclosed here, though, those techniques do not utilize radar backscatter. Crack and anomaly detectors that employ the use of eddy currents, for example, include the waste storage tank probe/scanner produced by ZETEC™ and the logging and survey tools marketed by TUBOSCOPE PIPELINE SERVICES™ (See: ZETEC™ INC., "Waste Storage Tank Probe/Scanner—Remote Field Testing (RFT) Probes", and "Introduction to Pipeline Services", "Survey Tool Operation" and "TruRes"). Eddy current and ultrasonic Lamb-wave techniques have been studied, and various combinations of pancake-coil arrays have been investigated and described in reports from Argonne National Laboratory. (See: D. R. Diercks, et al., "Overview of Steam Generator Tube Degradation and Integrity Issues", Argonne National Laboratory, Argonne, Ill.; S. Bakhtiari, et al., "Modeling of Eddy Current Probe Response for Steam Generator Tubes", Energy Technology Division, Argonne National Laboratory, Argonne, Ill.; and D. S. Kupperman, et al., "Characterization of Flaws in a Tube Bundle Mock-up for Reliability Studies", Argonne National Laboratory, Argonne, Ill.)

The concept of the present invention, by contrast, offers a technically different approach. Radar backscatter represents an improvement over existing technology because it offers the same or better resolution with respect to crack location and mapping than current methods while not requiring external components such as magnets (some eddy-current systems), immersion in water (some ultrasonic systems), or mechanical steering (pancake-coil systems). Likewise, the radar backscatter method of the present invention operates where a pulse-type radar system cannot. The dimensions of boiler tubes and oil/gas pipelines, for example, would require such a high-frequency system that the thickness of the metal wall would completely absorb the electromagnetic field before the field could reach the exterior.

BRIEF SUMMARY OF THE INVENTION

The present invention utilizes the concept of radar backscatter to detect cracks and other anomalies in tubes by generating from within a tube a continuous electromagnetic wave from a transverse magnetic-dipole antenna, reflecting the wave off the external surface of the tube, receiving the reflected signal using a coaxial electric-dipole receiver designed and positioned so that crosstalk between the transmitting and receiving antennas is minimized, and analyzing the return signal for signs of a tube anomaly.

Accordingly, an advantage of the present invention is that it provides a method for detecting anomalies in a tube or other enclosure which method utilizes the concept of radar backscatter.

Another advantage of the present invention is that it provides an apparatus for detecting anomalies in a tube or other enclosure which apparatus comprises a transverse magnetic dipole source and a coaxial electric-dipole receiver.

Yet another advantage of the present invention is that it provides an apparatus for detecting structural anomalies in a tube, a portion of the tube defining a longitudinal axis coincident with a z-axis of a Cartesian coordinate system comprising an x-axis, a y-axis and a z-axis, the apparatus comprising a transmitter generating a continuous-wave electric field within the tube, the electric field being parallel to the z-axis, the null of the electric field being located in the z-axis; and a receiver being located in the null receiving a backscattered signal from the tube, wherein anomalies in the tube cause a detectable change in said backscattered signal.

Another advantage of the present invention is that it provides a method for detecting structural anomalies in a tube, a portion of which defines a longitudinal axis coincident with a z-axis of a Cartesian coordinate system comprising an x-axis, a y-axis and a z-axis, the steps comprising transmitting a continuous-wave electric field parallel to the z-axis; generating a backscattered signal from the electric field off the tube; and receiving the backscattered signal with an internal receiver.

These and other advantages and objects of the present invention are fulfilled by the claimed invention in which the receiving antenna is a short electric dipole (ED) aligned with the axis of a tube which is also the z-axis of a Cartesian coordinate system. In the preferred embodiment, the transmitting antennas are a pair of orthogonal magnetic dipoles (MDs) which are centered at the coordinate origin and with moments along the x-axis and y-axis, respectively. (Throughout this disclosure, the term "short" in short electric dipole means much less than a wavelength in the surrounding medium.) The $E_z$-field from a MD whose moment is along the x-axis is applicable to both dielectric or conductive host media. The ED is located in the null of the $E_z$-field of the MD to minimize crosstalk, and the ED may also be offset along the z-axis as a matter of practical construction. The currents in the orthogonal MDs can be weighted so that a bi-lobed, combined $E_z$-beam can be steered in the azimuth to illuminate the interior of the tube wall in uniform angular increments. A target having a diameter of only 254 microns is detectable. This is not necessarily a lower limit to the minimum size, but merely an example.

DETAILED DISCUSSION

Introduction

Figure 1:
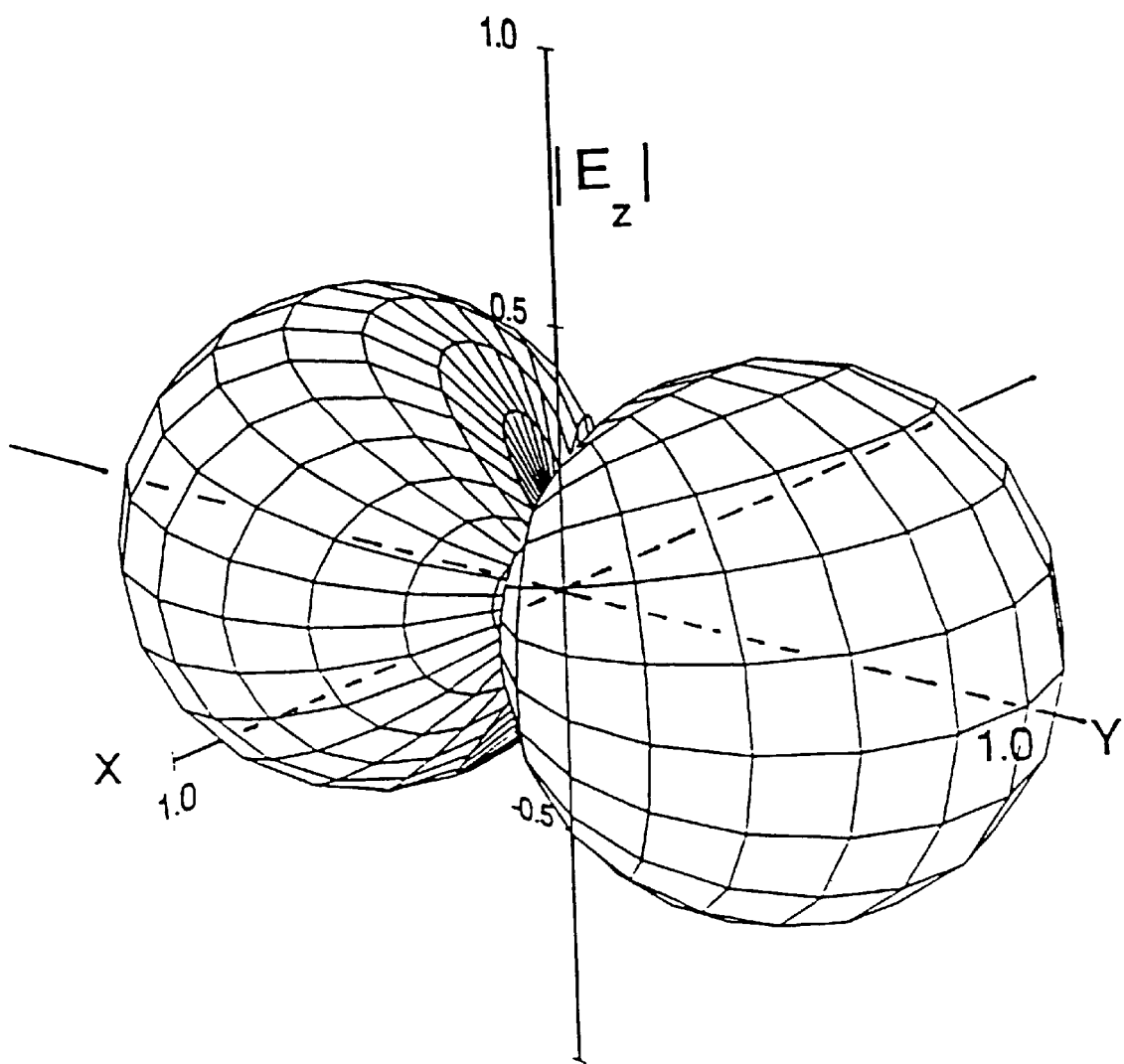
FIG. 1 is a graphic representation of the relative $|E_z\text{-field}|$ from an x-directed magnetic dipole at any spherical radius greater than zero.

The basic idea is to transmit an electric field which is parallel to the axis of the tube, and which will reflect off the exterior wall and return to an internal receiver. It is assumed that the return from a crack-anomaly will be distinguishable from that of an acceptable part of the tube wall, and that the interior of the tube is filled with air. A pulse-type system cannot be used because the small dimensions of boiler tubes, whose inner diameters are generally 10 cm or less, would require such a high-frequency system that the thickness of the metal wall would completely absorb the electromagnetic field before the field could reach the exterior.

A single-frequency, continuous-wave system, in which the transmitting and receiving antennas are designed to minimize the crosstalk between them, is presented here. The cross-talk constitutes a 'self-clutter' which will set the lower bound to the signal-to-noise ratio of the system. The choice of operating frequency must fulfill these opposing criteria:

1. The frequency must be low enough that the round-trip attenuation along the two-way path in the metal will be small enough to allow a detectable returned signal level at the receiver. This attenuation constraint upon the frequency will ensure that the operating frequency is below the cutoff frequency of the cylindrical waveguide formed by the tube. In other words, the receiver will not be excited by a waveguide mode per se. As a practical matter, to ensure detectability, I require that the rms returned signal be at least twice as great as the rms level of the clutter.
2. The frequency must be high enough so that cracks of some specified minimum size can be detected.

These two criteria are not separable, and, to make matters worse, the fractional amount of the field incident upon an anomaly that will be returned toward the interior of the tube is not yet known. It is assumed that this scattering loss is fixed at 1/100 (−40 dB) for present purposes.

One way to examine the effect of both frequency and clutter is to compare the magnitude of the field transmitted into the tube wall, attenuated by the both path loss and scattering loss, with the magnitude of the self-clutter field. This signal-to-clutter ratio, or SCR, can be written as follows:

$$E_{signal,rms} = E_{transmit,rms}\left(\frac{e^{-\frac{2d}{\delta}}}{100}\right), \quad (1)$$

where d=wall-thickness of the tube, and δ=the skindepth (later defined). The SCR is defined as $$SCR(\text{dB}) = 20\text{Log}\left(\frac{E_{signal,rms}}{E_{clutter,rms}}\right), \quad (2)$$

which becomes:

$$SCR(\text{dB}) = 20\text{Log}\left(\frac{E_{transmit,rms}}{E_{clutter,rms}}\right) - \frac{17.37d}{\delta} - 40, \quad (3)$$

In this formula the $2^{nd}$ term is the two-way path loss, the $3^{rd}$ term is the scattering loss, and $E_{transmit}$ and $E_{clutter}$ are computed according to Wait and Hill (See: James R. Wait and David A. Hill, 1977, *"Electromagnetic Fields of a Dipole Source in a Circular Tunnel Containing a Surface Wave Line"*, International Journal of Electronics, 1977, Vol. 42, No. 4, pp 377–391).

The target will be considered detectable only if the SCR is 6 dB or more. A discussion of the computation of the fields with application of the SCR to a metal boiler tube is given below.

The Primary Field

Because the use of an electric field parallel to the tube axis is considered, it is desirable to have a transmitter which not only provides such a field at the interior wall of the tube, but which also has an absence of such a field elsewhere in the tube where a receiving element could be placed.

Consider a Cartesian coordinate system in which the z-axis will later be placed along the axis of an air-filled tube. In the absence of the tube, the z-component of the electric field provided by an infinitesimal magnetic dipole whose moment is along the x-axis is given by:

$$E_z = \frac{-j\mu\omega IdA}{4\pi'}\sin\theta\sin\phi\left(\frac{jkR-1}{R^2}\right)e^{jkR}, \, V/m \quad (4)$$

where:

$$j=\sqrt{-1}$$

μ=permeability of free space, Henries/meter;
ω=2πf=radian frequency, seconds$^{-1}$;
k=α+j β=the propagation factor, meters$^{-1}$;

with $$\alpha = \frac{\omega\sqrt{\varepsilon r}}{c} \cdot \sqrt{\frac{+1+\sqrt{1+g^2}}{2}},$$

$$\beta = \frac{\omega\sqrt{\varepsilon r}}{c} \cdot \sqrt{\frac{-1+\sqrt{1+g^2}}{2}},$$

$$g = \frac{\sigma}{\omega\varepsilon_r\varepsilon_o} = \text{the loss tangent};$$

$\varepsilon_o$ = the dielectric constant of free space, Farads/m;

$\varepsilon_r$ = the relative dielectric constant;

$\sigma$ = conductivity, Siemens/m;

$c$ = speed of electromagnetic propagation in free space, m/s;

$I$ = dipole current, peak Amperes;

$dA$ = dipole area, meter$^2$;

and $(R, \theta, \phi)$ are the usual spherical coordinates. This formula for $E_z$ is not defined at the origin, R=0, where the magnetic dipole is located. The magnitude of $E_z$ is a maximum in the plane $\theta$=90° and along the direction $\phi$=±90°, and is zero whenever either $\theta$ or $\phi$ are either 0° or 180°. In the Cartesian coordinates, $E_z$ is a maximum along the ±y-axis and is zero in the xz-plane aside from the origin. An infinitesimal electric dipole, aligned parallel to the z-axis and placed anywhere in the xz-plane, aside from the origin, would be completely uncoupled from the transmitter. However, a physical dipole will always have a non-zero cylindrical radius, and its effect on self-clutter will be examined later.

If the magnitude of $E_z$ is written-out, the terms in R may be collected into one factor, and the angular distribution of $|E_z|$ is seen to be the same for any spherical radius greater than zero:

$$|E_z| = \frac{\mu\omega IdA}{4\pi}\left(\frac{\sqrt{(\alpha R)^2 + (1+\beta R)^2}}{R^2}\exp(-\beta R)\right)|\sin\theta||\sin\phi| \quad (5)$$

This distribution is shown in FIG. 1 in which the half-power beamwidth of each lobe is 90°. The bi-lobed distribution describes the primary field even when the magnetic dipole is enclosed by a cylindrical metal tube of radius 'ρ' as long as R≦ρ.

The Total Field within the Tube

The theory of the total field within a metal tube is described in following the example below. The z-component of the internal electric field is the sum of the primary field from the magnetic dipole, $E_{PRIMARY}$, and the field reflected from the wall, $E_{REFLECTED}$ $$E_z = E_{PRIMARY} + E_{REFLECTED} \quad (6)$$

The field transmitted into the tube wall, $E_{TRANSMIT}$, or $E_T$, is equal to $E_z$ evaluated at the interior air/tube boundary because of the continuity of the tangential components of the E-field. In a metal tube, at frequencies below the infrared, the parts of the propagation constant are equal to each other, namely $\alpha=\beta=\sqrt{\mu\omega\sigma/2}$, and attenuation through the wall thickness 'd' occurs as $\exp(-d/\delta)$ where $\delta$ is the 'skindepth' given by $\delta=1/\alpha$.

EXAMPLE

An Inconel tube with an inner diameter of 2.2 cm, a wall-thickness of 0.127 cm, and a conductivity of 8.2E5 S/m is typical of the smallest tube commonly found in boilers. The frequency of 47.88 KHz will be used to make the two-way path through the wall equal to one skindepth so that the second term in Eq.(3) becomes −8.7 dB. In the following figures, the fields will be presented as normalized surfaces in cylindrical coordinates in which radial distances are relative to the tube radius. The increments of normalized radius and polar angle will be 0.1 and 10° respectively.

Figure 2:
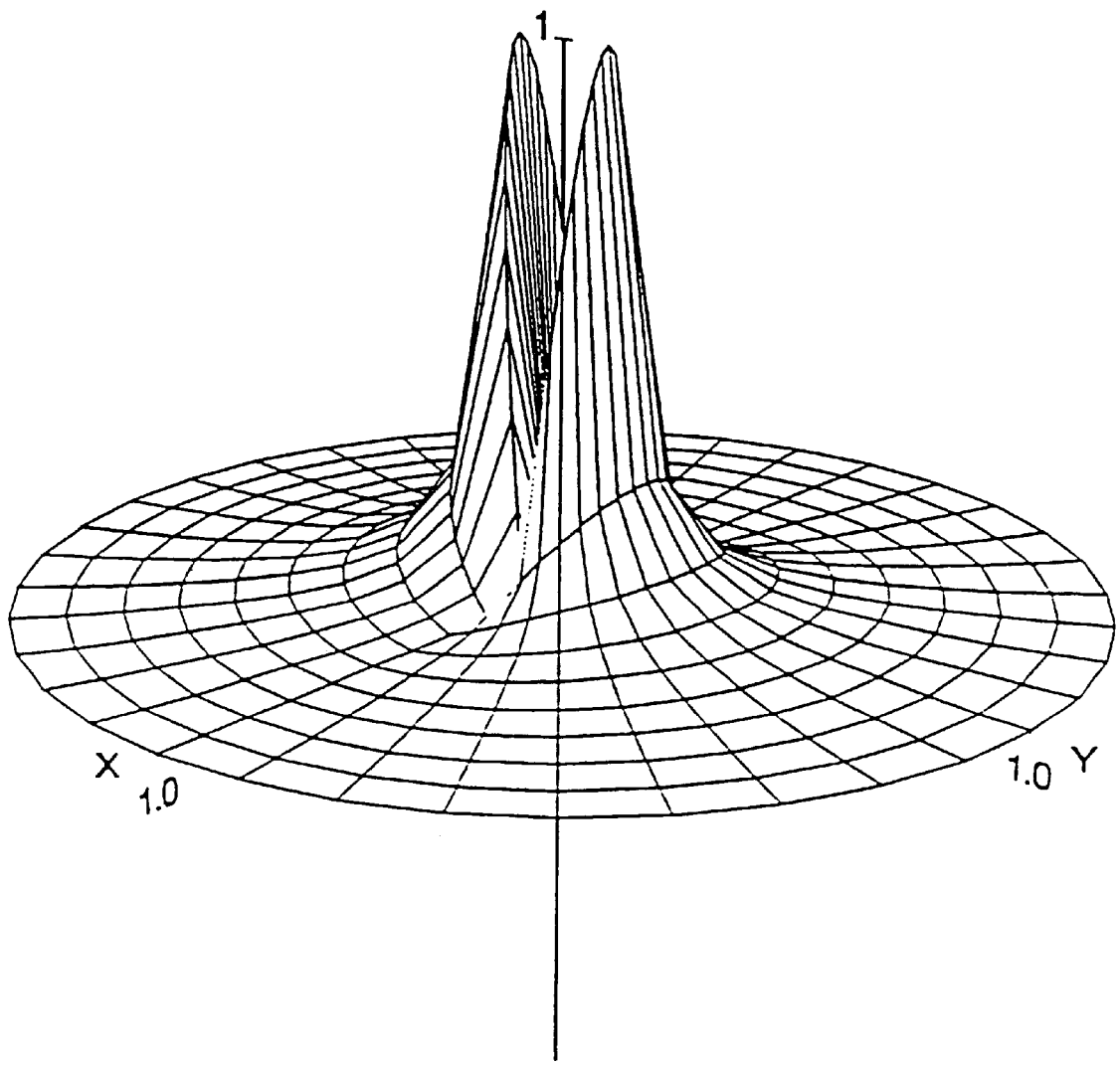
FIG. 2 is a graphic representation of the relative $E_z$-field within a 2.2 cm metal tube at z=0.

FIG. 2 illustrates the relative magnitude of $E_z$ in the xy-plane. The figure is dominated by the double-peaks near the z-axis. These occur because the field is computed ever more closely to the magnetic dipole located at the origin (where the graph is set to zero for display purposes). When the field along the tube wall at p=1 is examined closely, the field is seen to vary as the cosine of the polar angle rather than as the sine-function of the primary field, Eq.(4). This effect is caused by the large loss tangent which occurs in the metal tube. A small, z-oriented, electric dipole placed anywhere within FIG. 2 would be excited by strong $E_z$-fields, and provide a large self-clutter.

Figure 3:
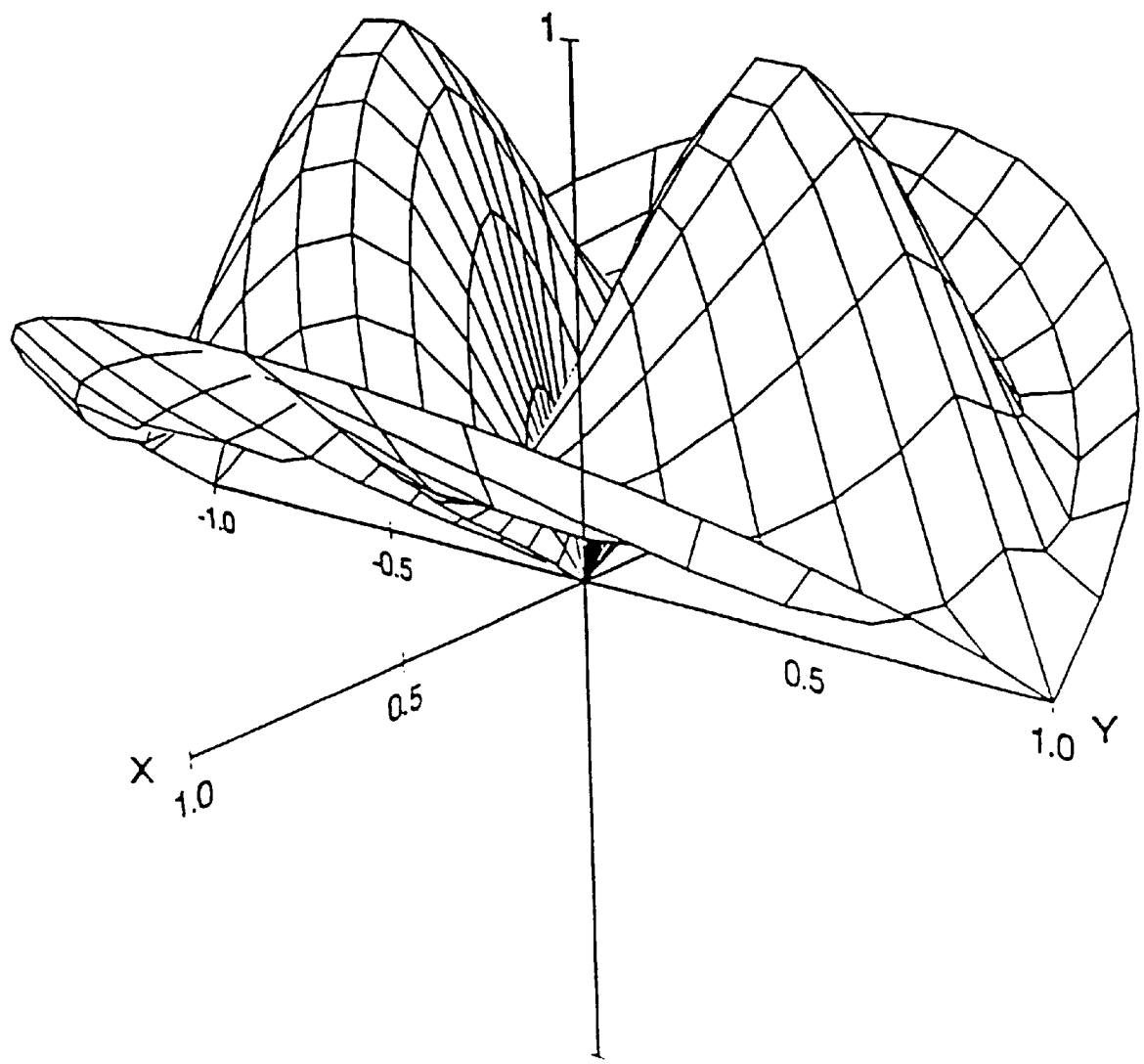
FIG. 3 is a graphic representation of the relative $E_z$-field within a 2.2 cm metal tube at z=1.1 cm.

FIG. 3 shows the relative magnitude of $E_z$ in the plane where Z is one tube radius. The cosine-nature of the field along the boundary is now very apparent. The surface varies rapidly, but the z-axis could be considered as a location for the receiving antenna.

Figure 4:
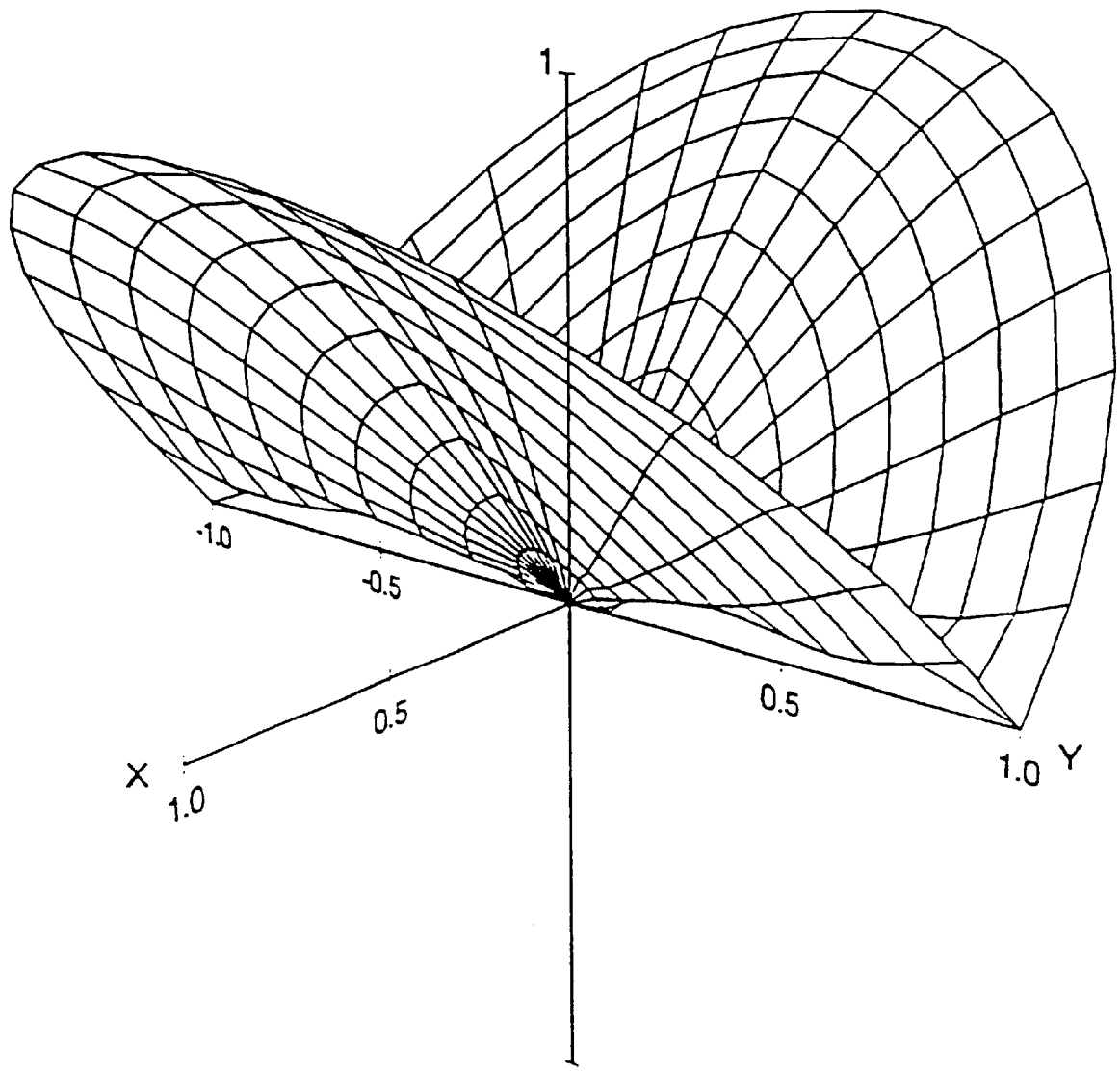
FIG. 4 is a graphic representation of the relative $E_z$-field within a 2.2 cm metal tube at z=2.2 cm.
Figure 5:
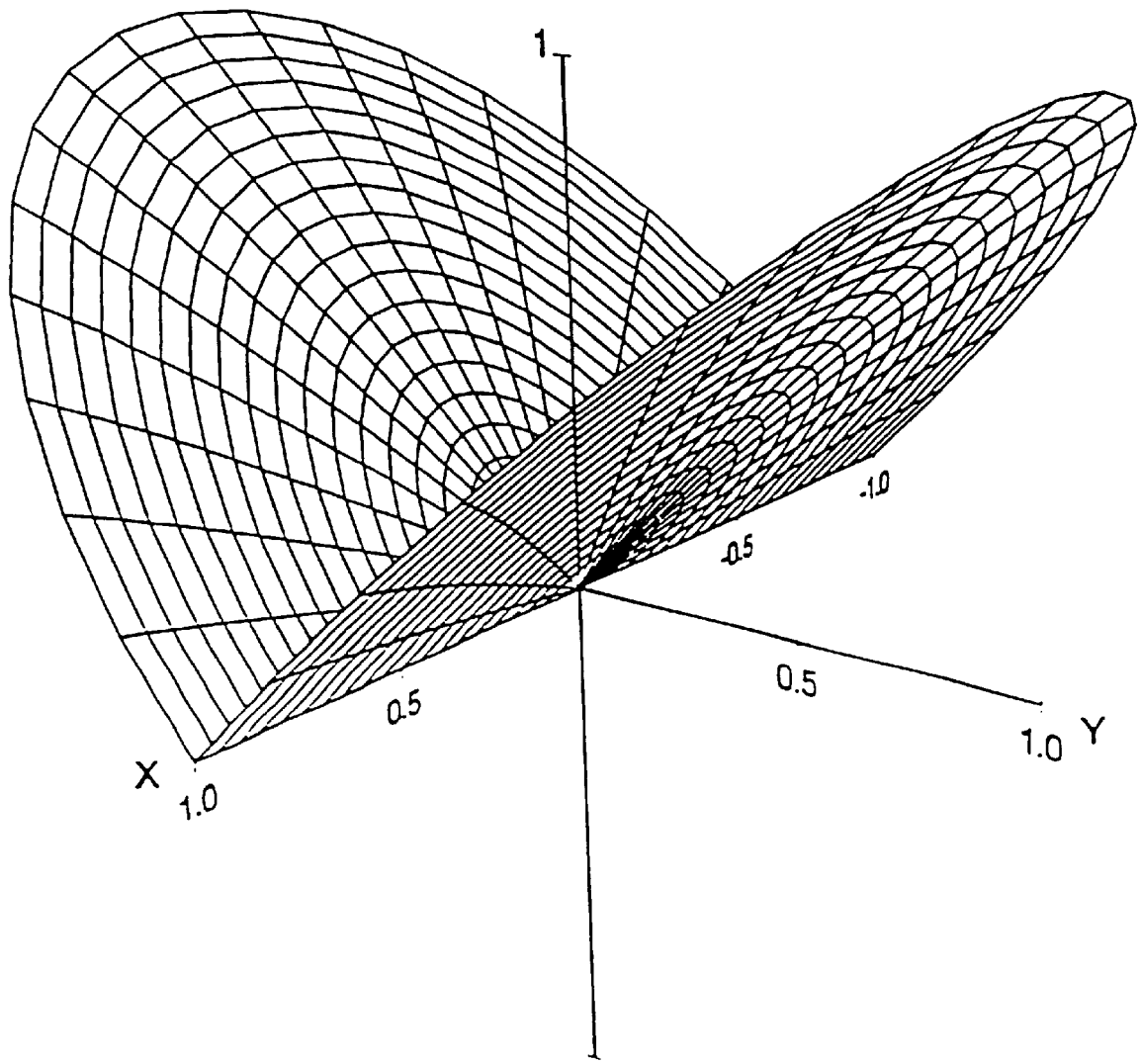
FIG. 5 is a graphic representation of the relative primary $E_z$-field within a 2.2 cm air tube at z=2.2 cm.

FIG. 4 shows the relative magnitude of $E_z$ in the plane where Z is one tube diameter. The surface appears as a folded disc, curved slightly downward at the outer edge, and with an undulation along the y-axis which falls to zero at the center and at Y=±1. The primary field alone is shown in FIG. 5, and, by comparison with FIG. 4, vividly demonstrates the rotation due to the reflecting boundary.

Suppose a small electric dipole, with a radius of one-tenth the tube radius, is placed at the origin in FIG. 4. The self-clutter field at the receiver is estimated as the mean value of the field along ρ=0.1. Suppose further that a crack is located along the exterior tube wall in the xy-plane which is also the location of the source at Z=0. The ratio of $E_{TRANSMIT}$ to $E_{CLUTTER}$, the first term in Eq.(3) is about 43.6 dB, but the SCR is −5.1 dB which is below the detectability criteria. Any other z-location of a crack will further reduce the SCR. For example, if the crack is located at Z=one tube radius, the $E_T$ field is reduced by 3 dB because of the beamwidth of the primary field, and the SCR decreases to −8.1 dB.

The problem is that the reflected field does not sufficiently reduce the primary field at the location of the receiving antenna. For example, using FIGS. 4 and 5, the ratio of the self-clutter field with the tube present, to the field with the tube absent, is only −12.6 dB. There are three changes that can be made:

Increase the antenna separation distance

Change the operating frequency

Reduce the diameter of the electric dipole.

Distance. Increasing the antenna separation distance is dubious for two reasons: The allowance for the scattering loss would have to be increased because of the greater scattering angle, and the increased path length in the metal would further decrease the signal because of the exponential attenuation.

Frequency. If the frequency is increased by a factor of 4, the $E_T$ field increases by 7.3 dB, but the skin depth is halved and the path loss increases by 8.7 dB. The self-clutter increases by about 5.4 dB, and the net result is that the SCR decreases from −5.1 dB to −11.9 dB. If the frequency is decreased by a factor of 4, the $E_T$ field decreases by 8.4 dB, but the skin depth is doubled and the path loss decreases by 4.3 dB. The self-clutter decreases by 5.5 dB, and the net result is that the SCR decreases from −5.1 dB to −3.6 dB. By how much can the frequency be decreased in an effort to raise the SCR to 6 dB? This question cannot be answered without a model library of cracks and their scattering loss, but the scattering loss will eventually increase with decreasing frequency as the maximum dimension of the crack becomes a smaller fraction of the wavelength in the metal.

Dipole Diameter. In the present example the diameter of the electric dipole is taken as one-tenth the inner diameter of the tube or 0.22 cm. Reducing the dipole thickness by a factor of four with the use of printed circuit techniques, and coupling directly to an integrated preamplifier, would raise the SCR from −5.1 dB to 6.9 dB and make the crack detectable.

Electromagnetic Fields in a Cylindrical Void within a Complex Media

The solution for the electromagnetic fields within a borehole surrounded by a complex homogeneous medium was included by J. R. Wait and David A. Hill as part of an article devoted to another topic (Wait and Hill, id). The theory is summarized below with the authors' notation in which time-harmonic fields are assumed in accordance with exp (jωt).

Figure 6:
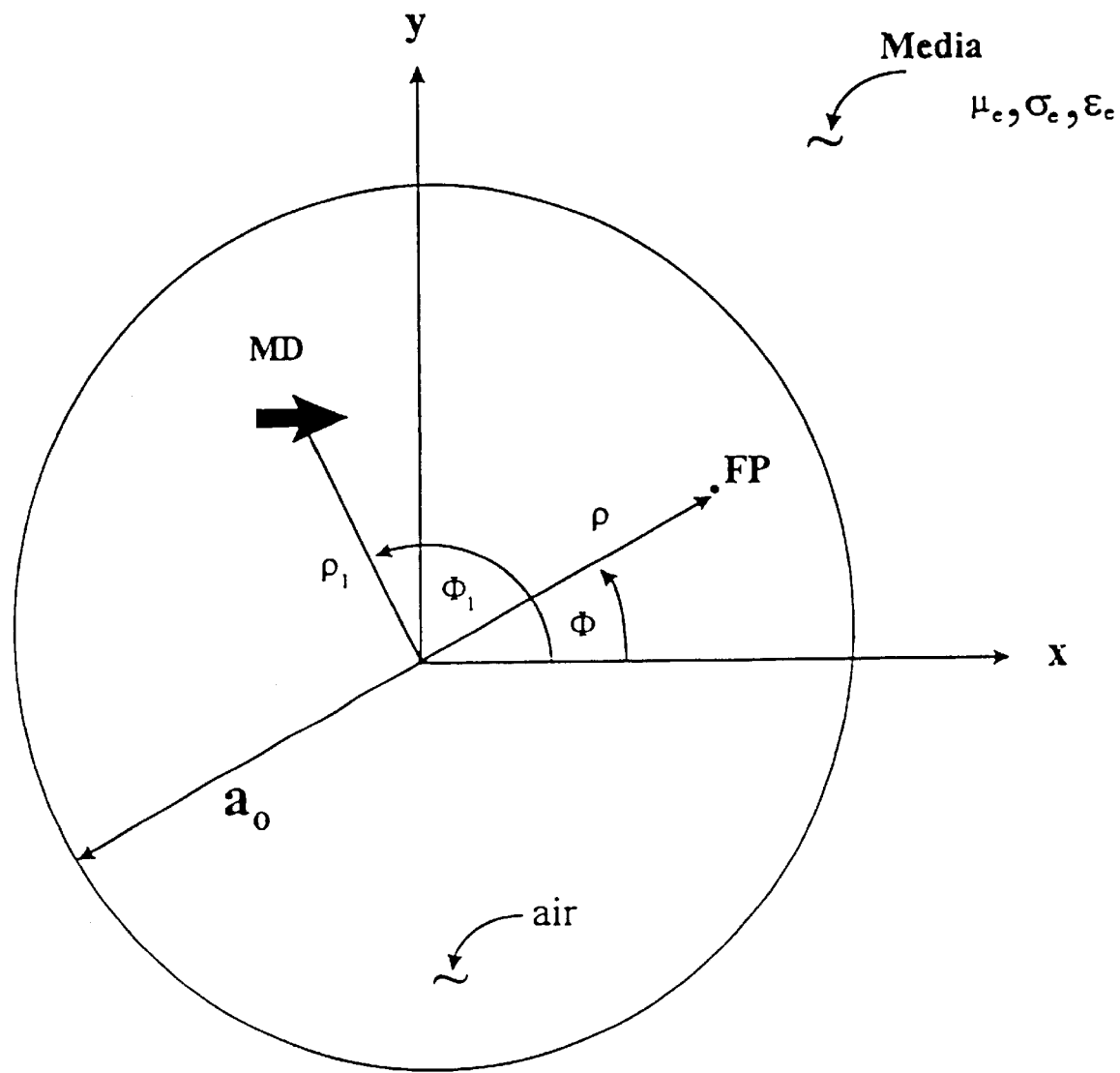
FIG. 6 is a graphic representation of cross-section geometry for a cylindrical void.

Geometry. FIG. 6 depicts the xy-plane intercepted by a circular cylinder of radius '$a_o$' whose axis is coincident with the z-axis. A magnetic dipole, with its moment parallel to the x-axis, is located at cylindrical coordinates $(\rho_1,\phi_1,0)$ where $\rho_1 < |a_o|$, and the field point is at $(\rho,\phi,z)$ with $\rho < a_o$. The cylinder is air-filled with permeability $\mu_o$ and dielectric constant $\epsilon_o$, and the surrounding homogeneous media has conductivity $\sigma_e$ with permeability $\mu_e$ and dielectric constant $\epsilon_e$.

$E_z$ Field. The $E_z$ field is represented as a superposition of modes in terms of the Hertz potentials which supply the modal contributions:

$$E_Z = \sum_{m=-\infty}^{+\infty} \int_{-\infty}^{+\infty} -v^2 \{A_m(\lambda)K_m(v\rho) + P_m(\lambda)I_m(v\rho)\} \exp[-jm(\phi-\phi_1)]\exp(-j\lambda z)\,d\lambda \quad (A1)$$

where $I_m(v\rho)$ and $K_m(v\rho)$ are modified Bessel functions, $v^2 = \lambda^2 + \gamma_o^2$ and $\gamma_o = j\omega/c$. The functions $A_m(\lambda)$ and $B_m(\lambda)$ are the primary Hertz potentials determined by the strength and orientation of the magnetic dipole source, and the secondary potential $P_m(\lambda)$ is related to $A_m(\lambda)$ and $B_m(\lambda)$ by the boundary conditions at the cylinder/media interface.

Hertz Potentials. When the x-directed magnetic dipole is located at Z=0, the electric and magnetic Hertz potentials are given by these expressions when $\rho_1 < \rho$:

$$A_m(\lambda) = \frac{-\mu_o \omega I dA}{8v\pi^2}[I_{m-1}(v\rho_1)\exp(-j\phi_1) - I_{m+1}(v\rho_1)\exp(j\phi_1)]\ V\cdot m^2 \quad (A2)$$

and $$B_m(\lambda) = \frac{-j\lambda IdA}{8v\pi^2}[I_{m-1}(v\rho_1)\exp(-j\phi_1) + I_{m+1}(v\rho_1)\exp(j\phi_1)]\ A\cdot m^2 \quad (A3)$$

Boundary Conditions. The boundary conditions at the cylinder/media interface can be succinctly expressed in terms of a radial wave impedance $Z_m$ and a radial wave admittance $Y_m$ at $\rho=a_o$ (J. A. Stratton, 1941, "Electromagnetic Theory", McGraw-Hill, New York, pp 354–361, p532.):

$$E_{\phi m} = \alpha_m E_{zm} + Z_m H_{zm} \quad (A4)$$

$$H_{\phi m} = -Y_m E_{zm} + \alpha_m H_{zm} \quad (A5)$$

where:

$$\alpha_m = m\lambda/(a_o u^2) \quad (A6)$$

$$\gamma_e^2 = j\mu_e \omega(\sigma_e + j\omega\epsilon_e) \quad (A7)$$

$$u^2 = \lambda^2 + \gamma_e^2 \quad (A8)$$

$$Y_m = [j\gamma_e^2/(u\mu_e\omega)]K'_m(ua_o)/K_m(ua_o) \quad (A9)$$

$$Z_m = -(j\mu_e\omega/u)K'_m(ua_o)/K_m(ua_o) \quad (A10)$$

The application of the boundary conditions establish the relation of the secondary potential, $P_m$, to the primary potentials $A_m$ and $B_m$:

$$P_m = -[A_m(\lambda)r_m + B_m(\lambda)t_m]/D_m \quad V\cdot m^2 \quad (A11)$$

where $$r_m = \left[\left(\frac{m\lambda}{a_o v^2} - \alpha_m\right)^2 + \left(\frac{\gamma_o K'_m}{vK_m} + \eta_o Y_m\right)\left(\frac{\gamma_o I'_m}{vI_m} + \frac{Z_m}{\eta_o}\right)\right]I_m K_m \quad (A12)$$

$$t_m = \left(\frac{m\lambda}{a_o v^2} - \alpha_m\right)j\mu_o \frac{\omega}{a_o v^2} \quad (A13)$$

$$D_m = \left[\left(\frac{m\lambda}{a_o v^2} - \alpha_m\right)^2 + \left(\frac{\gamma_o I'_m}{vI_m} + \eta_o Y_m\right)\left(\frac{\gamma_o I'_m}{vI_m} + \frac{Z_m}{\eta_o}\right)\right]I_m^2 \quad (A14)$$

and $\eta_o = \sqrt{\mu_o/\epsilon_o}$ is assumed to be the characteristic impedance of the air inside the cylinder. The argument of the modified Bessel functions is $\alpha_o v$, and the prime, ' denotes differentiation with respect to $v$, the wavenumber within the cylinder.

Computational Notes. In the special case where the magnetic dipole is located at the origin, the representations of the Hertz potentials are simplified and only two modes are needed, namely m=±1. For example, Eq.(A2) for $A_m(\lambda)$ becomes:

$$A_m = A^o[I_{m-1}(0) - I_{m+1}(0)] \quad (A15)$$

with $A^o = -\mu_o \omega IdA4/(8v\pi^2)$. Using the properties of the Bessel functions (M. Abramowitz and I. A. Stegun, 1972, "Handbook of Mathematical Functions", Dover Publications Inc. New York, Sections 9.6.1–9.7.11), $A_{-1} = A^o$, and $A_{+1} = -A^o$, but $A_m$ is zero for m=0, m≦−2, and m≧2. Similarly, $B_{-1} = B^o$, and $B_{+1} = -B^o$ where $B^o$ is the leading factor, and all other $B_m$ are zero.

As a check on both the code and the theory, it is of interest to see what happens when $\gamma_e = \gamma_o$, or when $a_o \to \infty$. The secondary potential $P_m$ becomes zero as required, and the field reduces to:

$$E_Z = \sum_{m=\pm 1} \int_{-\infty}^{+\infty} -v^2\{A_m(\lambda)K_m(v\rho)\}\exp[-jm\phi]\exp[-j\lambda z]\,d\lambda \quad (A16)$$

The closed-form solution for the dipole source in air is given by:

$$E_z = \frac{-j\mu\omega IdA}{4\pi}\sin\theta\sin\phi\left(\frac{jkR-1}{R^2}\right)e^{jkR}. \quad (A17)$$

Eq.(A16) is undefined when p is zero, and Eq.(A17) is undefined when R is zero, because these respective radii would place the field-point at the location of the magnetic dipole.

Figure 7:
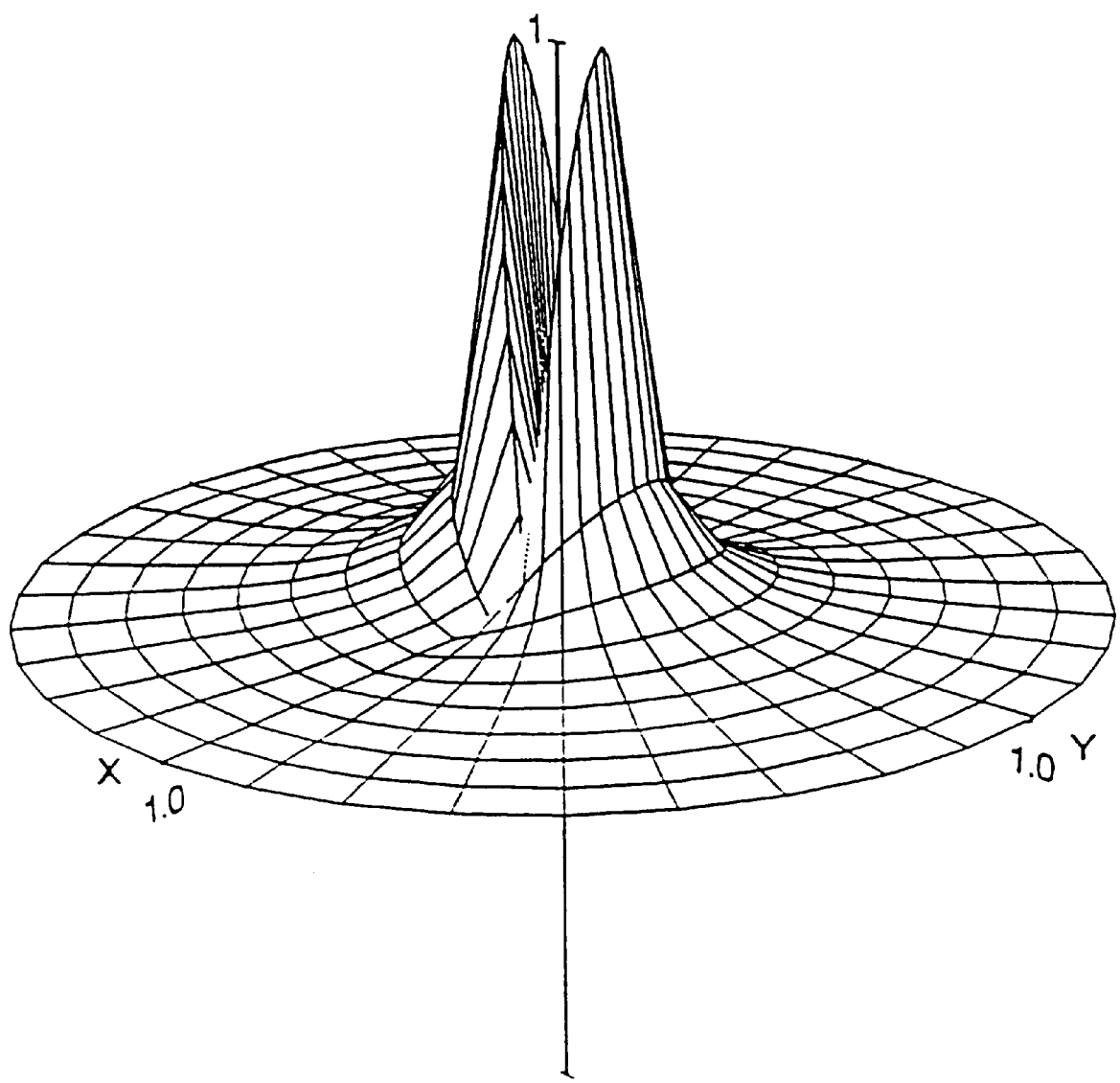
FIG. 7 is a graphic representation of the relative $E_z$-field in air within a radius of 1.1 cm in the xy-plane.
Figure 8:
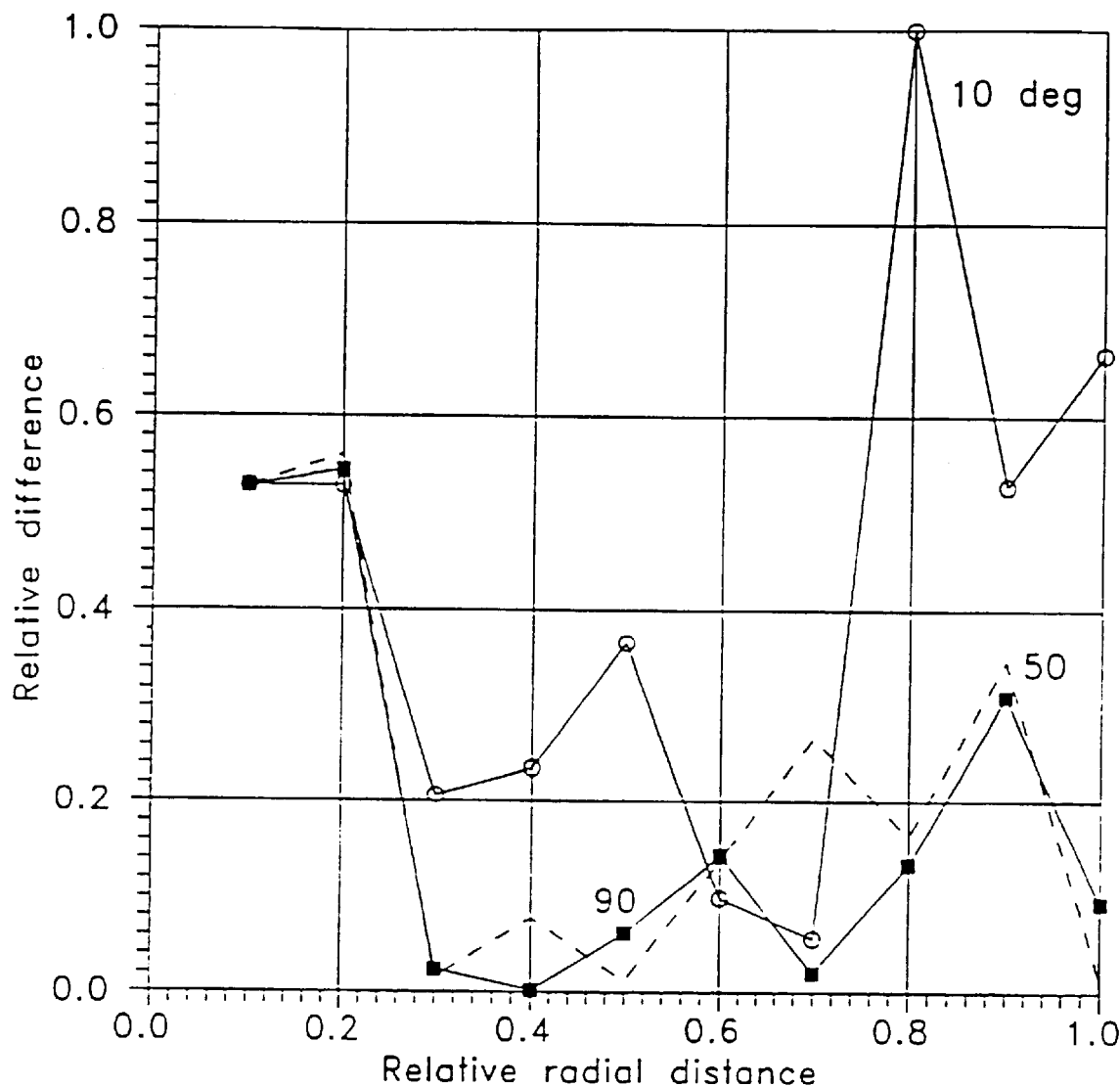
FIG. 8 is a graphic representation of the difference between computations with azimuth as a parameter, maximum difference=1/2075.

As a check, the magnitudes of these two formulas were compared for a frequency of 47.88 KHz and p=1.1 cm in the xy-plane. The magnitude-plots overlap as shown in FIG. 7 where the figure is dominated by double-peaks near the z-axis. These occur because the field is computed ever more closely to the magnetic dipole located at the origin (where the graph is set to zero for display purposes). Along the rim of the figure, where the normalized radius is one, the magnitude varies as $|\sin(\phi)|$ with maximums at 90° and 180° as required by Eq.(A17). The maximum difference between the two formulas is about 0.045% and is shown in FIG. 8 (max. diff.=1/2075). This relative accuracy of less than one-percent is sufficient for practical purposes.

Conclusion

Numerical computations of the fields show that the use of a printed-circuit receiving dipole and integrated amplifier could detect cracks whose scattering loss is not less than –40 dB. It would be desirable to develop a catalog of practical cracks which are found in a variety of pipe sizes and conductivities. A three-dimensional model code (See: G. A. Newman and D. L. Alumbaugh, 1996, "Electromagnetic Modeling of Subsurface 3D Structures", Proceedings of the 1996 IEEE International Geoscience and Remote Sensing Symposium, Vol. IV, pp 1941–1944, Lincoln, Nebr., May 1996. IEEE #96CH3587; and G. A. Newman and D. L. Alumbaugh, 1996, "Three-Dimensional Electromagnetic Modeling and Inversion on Massively Parallel Computers", Sandia National Laboratories report SAND96-0582, March 1996.) could be used as a means of estimating the scattering loss of each catalog entry. The design and development of an instrument could be undertaken if the modeling showed that practical cracks have scattering losses greater than –40 dB.

Figure 9:
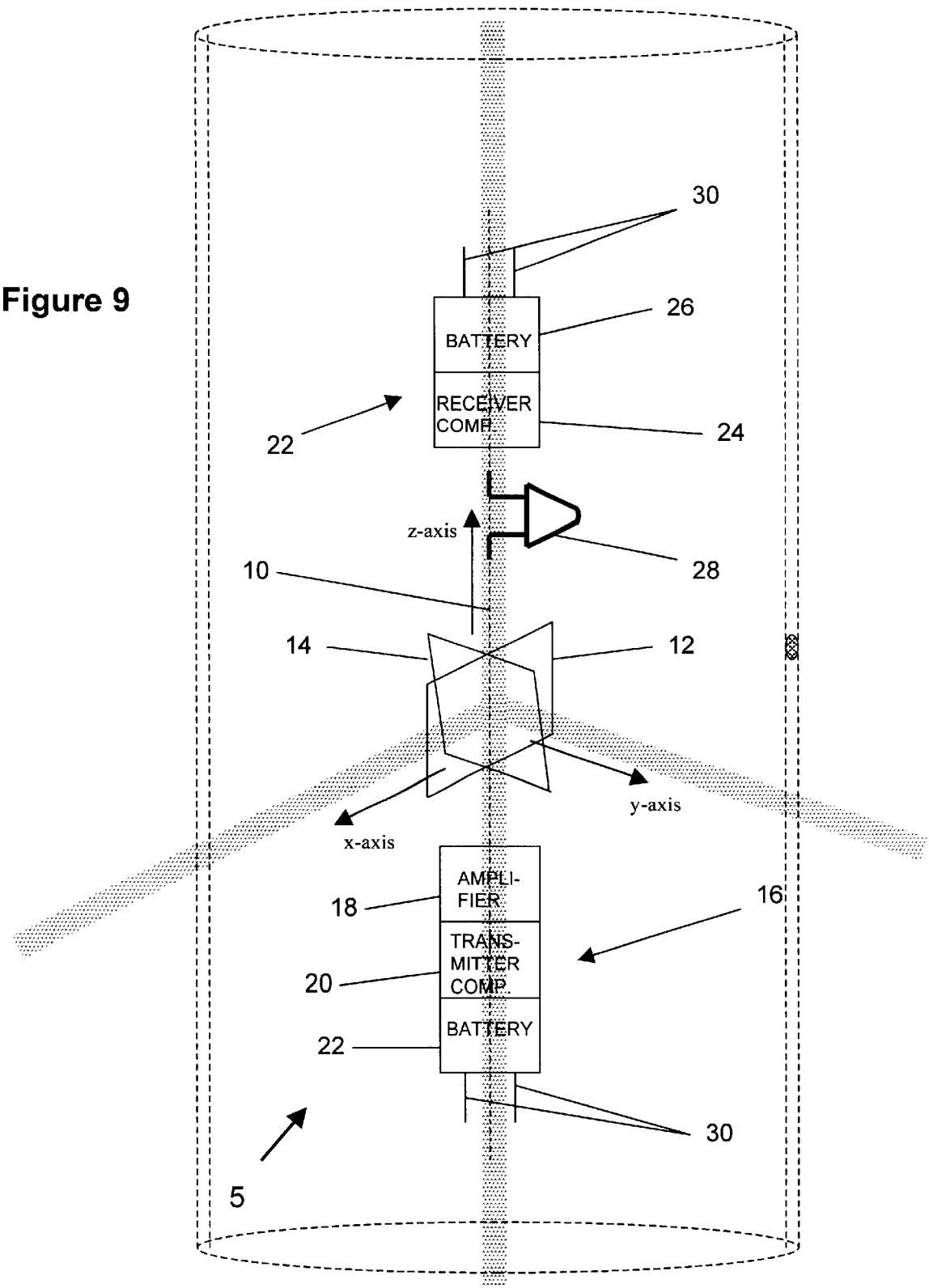
FIG. 9 is a schematic representation of the elements of a probe apparatus embodying the principles of the invention.

FIG. 9 presents a schematic representation of the preferred embodiment of the present invention. The elements comprising the detector assembly 5 are shown positioned along a tube axis 10, which is coincident with the z-axis of a Cartesian coordinate system. Two crossed loops, 12 and 14, represent a pair of orthogonal magnetic dipoles, one having its moment oriented along the x-axis of the Cartesian coordinate system, and the other having its moment oriented along the y-axis of the Cartesian coordinate system. Also shown is a transmitter 16 in operative association with the loops 12, 14 which in the preferred embodiment is positioned generally in alignment with the tube axis 10 and to one side of the crossed loops 12, 14. The transmitter 16 in the preferred embodiment comprises a Class D amplifier 18, transmitter components 20 (including sync, control and FOL), and a transmitter battery (or batteries) 22. On the other side of the crossed loops 12, 14 is a receiver 22, likewise positioned generally in alignment with the tube axis 10, the receiver 22 comprising receiver components 24 (including sync, control and FOL) and a receiver battery (or batteries) 26. Also in the preferred embodiment is an integrated printed circuit electric dipole and preamplifier 28 in operative association with the other receiver components 24. Finally, shown in the Figure are pull cables 30 attached to either end of the assembly 5. The pull cables in the preferred embodiment are manufactured from Kevlar™ or other similar material and each comprise two fiber optic links for communication outside of the tube. The transmitter 16 generates a continuous-wave electric field within the tube, that electric field being parallel to the tube axis 10, with the null of the electric field located in the tube axis 10. The receiver 22 is located in that null and receives a backscattered signal from the tube. Anomalies in the tube cause changes in the backscattered signal thereby allowing for detection of those anomalies.

The invention being thus described, it will be obvious that the same may be varied in many ways. Such variations are not to be regarded as a departure from the spirit and scope of the invention, and all such modifications as would be obvious to one skilled in the art are intended to be included within the scope of the appended claims.

I claim:

1. An apparatus for detecting structural anomalies in a tube, a portion of said tube defining a longitudinal axis coincident with a z-axis of a Cartesian coordinate system comprising an x-axis, a y-axis and a z-axis, the apparatus comprising:

a transmitter generating a continuous-wave electric field within said tube, said electric field being parallel to said z-axis, and having a null, said null located in said z-axis; and a receiver located in said null receiving a backscattered signal from said tube, wherein anomalies in said tube cause a detectable change in said backscattered signal.

2. The apparatus of claim 1 wherein said tube is metallic.

3. The apparatus of claim 1 wherein said tube is right circular cylindrical.

4. The apparatus of claim 1 wherein said transmitter comprises a transverse magnetic-dipole source.

5. The apparatus of claim 4 wherein said transverse magnetic-dipole source comprises a pair of orthogonal magnetic dipoles.

6. The apparatus of claim 5, wherein said pair of orthogonal magnetic dipoles are centered at a coordinate origin of said Cartesian coordinate system.

7. The apparatus of claim 6 wherein a first moment of said pair of orthogonal magnetic dipoles is oriented along said x-axis and a second moment of said pair of orthogonal magnetic dipoles is oriented along said y-axis.

8. The apparatus of claim 1 wherein said receiver comprises a coaxial electric-dipole.

9. The apparatus of claim 8 wherein said coaxial electric-dipole comprises a short electric dipole.

10. The apparatus of claim 9 wherein said short electric dipole is aligned with and along said z-axis.

11. A method for detecting structural anomalies in a tube, a portion of which defines a longitudinal axis coincident with a z-axis of a Cartesian coordinate system comprising an x-axis, a y-axis and a z-axis, the steps comprising:

transmitting a continuous-wave electric field parallel to said z-axis;

generating a backscattered signal from said electric field off said tube; and receiving said backscattered signal with a receiver being located at a null.

12. The method of claim 11 wherein said tube is metallic.

13. The method of claim 11 wherein said tube is right circular cylindrical.

14. The method of claim 11 wherein an operating frequency of said electric field is below a cutoff frequency of a cylindrical waveguide formed by said tube and a wavelength of said operating frequency is smaller than a physical dimension of an anomaly in said tube.

15. The method of claim 14 wherein said physical dimension is parallel to said z-axis.

16. The method of claim 11 wherein a cross-talk constituting a self-clutter between a transmitter generating said continuous-wave electric field and said receiver sets a lower bound to a signal-to-noise ratio.

17. The method of claim 16 wherein said signal-to-noise ratio of a detectable anomaly in said tube is equal to or greater than 6 dB.

18. The method of claim 11, wherein a transmitter generating said continuous-wave electric field comprises a transverse magnetic-dipole source.

19. The method of claim 18 wherein said transverse magnetic-dipole source comprises a pair of orthogonal magnetic dipoles.

20. The method of claim 19 wherein said pair of orthogonal magnetic dipoles are centered at a coordinate origin of said Cartesian coordinate system.

21. The method of claim 20 wherein a first moment of said pair of orthogonal magnetic dipoles is oriented along said x-axis and a second moment of said pair of orthogonal magnetic dipoles is oriented along said y-axis.

22. The method of claim 11 wherein said receiver comprises a coaxial electric-dipole.

23. The method of claim 22 wherein said coaxial electric-dipole comprises a short electric dipole.

24. The method of claim 23 wherein said short electric dipole is aligned with and along said z-axis.

25. A method for detecting structural anomalies in a right circular cylindrical tube, a portion of which defines a longitudinal axis coincident with a z-axis of a Cartesian coordinate system comprising an x-axis, a y-axis and a z-axis, the steps comprising: transmitting a continuous-wave electric field parallel to said z-axis said continuous-wave electric field being generated by a transmitter, said transmitter comprising a pair of orthogonal magnetic dipoles centered at a coordinate origin of said Cartesian coordinate system and having a first moment oriented along said x-axis and a second moment oriented along said y-axis, wherein an operating frequency of said electric field is below a cutoff frequency of a cylindrical waveguide formed by said tube and wavelength of said operating frequency is smaller than a dimension of an anomaly in said tube, said dimension being parallel to said z-axis;

generating a backscattered signal from said electric field off said tube; and receiving said backscattered signal with an receiver, said receiver comprising a short electric dipole aligned with and along said z-axis, wherein a cross-talk constituting a self-clutter between said transmitter and said receiver sets a lower bound to a signal-to-noise ratio at 6 dB.

26. An apparatus for detecting structural anomalies in a right circular cylindrical tube, a portion of said tube defining a longitudinal axis coincident with a z-axis of a Cartesian coordinate system comprising an x-axis, a y-axis and a z-axis, the apparatus comprising:

a pair of orthogonal magnetic dipoles centered at a coordinate origin of said Cartesian coordinate system and having a first moment oriented along said x-axis and a second moment oriented along said y-axis, said pair of orthogonal magnetic dipoles generating a continuous-wave electric field within said tube, said electric field being parallel to said z-axis, and having a null, said null located in said z-axis of said electric field; and a short electric dipole receiver aligned with and along said z-axis, said short electric dipole receiver located in said null and receiving a backscattered signal from said tube, wherein anomalies in said tube cause a detectable change in said backscattered signal.

* * * * *